United States Patent [19]

Butter et al.

[11] Patent Number: 4,588,848

[45] Date of Patent: May 13, 1986

[54] SYNTHESIS OF NEOALKANOLS

[75] Inventors: Stephen A. Butter, Allentown; Ilse Stoll, Bethlehem, both of Pa.

[73] Assignee: Air Products and Chemicals, Inc., Allentown, Pa.

[21] Appl. No.: 667,047

[22] Filed: Nov. 1, 1984

[51] Int. Cl.[4] .................. C07C 29/136; C07C 31/125
[52] U.S. Cl. ..................... 568/885; 502/342
[58] Field of Search ........................ 568/885

[56] References Cited

U.S. PATENT DOCUMENTS

| | | | |
|---|---|---|---|
| 1,839,974 | 1/1932 | Lazier | 568/885 |
| 2,091,800 | 8/1937 | Adkins et al. | 568/885 |
| 2,110,483 | 3/1938 | Guyer et al. | 568/885 |
| 2,275,152 | 3/1942 | Lazier | 568/885 |
| 2,340,688 | 2/1944 | Richardson et al. | 568/884 |
| 2,549,416 | 4/1951 | Brooks | 568/885 |
| 2,607,807 | 8/1952 | Ford et al. | 568/885 |
| 2,986,577 | 5/1961 | Kurhajec | 568/885 |
| 3,197,418 | 7/1965 | Maebashi et al. | 568/885 |
| 3,361,832 | 1/1968 | Pine et al. | 568/885 |
| 3,478,112 | 11/1969 | Adam et al. | 568/885 |
| 3,920,766 | 11/1975 | Jubin, Jr. et al. | 585/733 |
| 3,923,694 | 12/1975 | Cornthwaite | 252/463 |
| 3,961,037 | 6/1976 | Davies et al. | 423/656 |
| 3,985,814 | 10/1976 | Dougherty | 568/876 |
| 4,104,478 | 8/1978 | Trivedi | 568/885 |
| 4,149,021 | 4/1979 | Wall | 568/885 |
| 4,279,781 | 7/1981 | Dienes et al. | 252/463 |
| 4,283,581 | 8/1981 | Wilkes | 568/864 |
| 4,398,039 | 8/1983 | Pesa et al. | 568/885 |
| 4,405,819 | 9/1983 | Duckwall, Jr. | 568/814 |
| 4,433,175 | 2/1984 | Kaufhold | 568/885 |
| 4,443,639 | 4/1984 | Pesa et al. | 568/885 |

FOREIGN PATENT DOCUMENTS

| | | | |
|---|---|---|---|
| 702753 | 1/1965 | Canada | 568/885 |
| 1021354 | 11/1977 | Canada | |
| 1150371 | 1/1963 | Fed. Rep. of Germany | 568/885 |
| 1154448 | 9/1963 | Fed. Rep. of Germany | 568/885 |
| 032237A | 2/1982 | Japan | |
| 03854 | 11/1982 | PCT Int'l Appl. | 568/885 |
| 768199 | 2/1957 | United Kingdom | 568/885 |
| 961337 | 6/1964 | United Kingdom | 568/885 |
| 899113 | 1/1980 | U.S.S.R. | |

OTHER PUBLICATIONS

Landa et al., *Chem. Listy*, vol. 51 (1957), 452–458, translation.
Adkins, *J. Am. Chem. Soc.*, vol. 72 (1950), 2626–2629.
Puzitskii et al., *Neftekhimiya*, vol. 7(2) (1967), 280–285, Chemical Abstract.
Shutikova et al., *Tr. Vses. Nauch.-Issled. Inst. Natur. Dushist. Veshchestv*, No. 7 (1965), 16–20, Chemical Abstract.
Vedage et al., *J. Catalysis*, vol. 77 (1982), p. 558.
Klier, "Methanol Synthesis," *Advances in Catalysis*, vol. 31 (1982), pp. 258–271.

*Primary Examiner*—J. E. Evans
*Attorney, Agent, or Firm*—Richard A. Dannells, Jr.; James C. Simmons; E. Eugene Innis

[57] ABSTRACT

Neoalkanols of the formula $R_1R_2R_3CCH_2OH$ are synthesized by hydrogenation of a neoacid of the formula $R_1R_2R_3CCOOH$, wherein $R_1$, $R_2$ and $R_3$ are the same or different alkyl of 1–10 carbon atoms, at a temperature of 175°–350° C. and a hydrogen pressure of 10–100 Kg/cm$^2$ over a copper oxide/zinc oxide hydrogenation catalyst.

10 Claims, 2 Drawing Figures

Pivalic Acid in Hexane Feed

Pivalic Acid in Methanol Feed

SYNTHESIS OF NEOALKANOLS

TECHNICAL FIELD

This invention relates to processes for the synthesis of neoalkanols from corresponding neoacids.

Neoalkanols are compounds of the formula $R_1R_2R_3CCH_2OH$. Typically, each R is alkyl of 1–10 carbon atoms. The lowest member of this series of compounds, in which each R is methyl, is neopentanol, $(CH_3)_3CCH_2OH$. Neopentanol and other neoalcohols are of commercial interest because they are used, for example, in the manufacture of plasticizers or lubricant bases or additives.

Neoacids should provide economically competitive starting materials for synthesis of relatively pure neoalkanols, such as neopentanol, by catalytic hydrogenation.

BACKGROUND ART

Duckwall, Jr., in U.S. Pat. No. 4,405,819, has proposed obtaining alcohols from acids, which can be branched, using a metal-containing hydrogenation catalyst. However, the process requires a sweep gas, containing carbon monoxide.

Wall has recited, in U.S. Pat. No. 4,149,021, the hydrogenation of esters, apparently of linear acids, using a cobalt/zinc/copper catalyst. The use of a copper/zinc oxide catalyst is said to be undesirable, because of catalyst instability.

Wilkes has disclosed, in U.S. Pat. No. 4,283,581, a process for hydrogenating feed stocks, such as glycolide and glycolates, to ethylene glycol, using a copper/zinc oxide catalyst, supported on silica. The reference indicates that, using a similar copper/zinc oxide/alumina catalyst, low conversions are obtained at about 190° C. and a pressure of 105 Kg/cm². Higher conversion (46%) was reported at a higher temperature.

The reduction of branched esters, e.g., pivalic acid esters, to alcohols, has been disclosed by Kurhajec in U.S. Pat. No. 2,986,577. A copper chromite catalyst was employed. The reaction required a high hydrogen pressure, of the order of 232 Kg/cm².

Pine et al. (U.S. Pat. No. 3,361,832) have accomplished conversion of branched acids, generally in the form of esters, to alcohols employing a molybdenum sulfide catalyst, under relatively low temperatures and pressures. However, for high selectivity toward corresponding alcohols, e.g., neoheptanol, the use of high pressures, well above about 70 Kg/cm², are required.

Landa et al., Chem. Listy, vol. 51 (1957), 452–458, have recited obtaining small amounts of neopentanol by hydrogenation of methyl pivalate, using Adkins' copper-chromium oxide catalyst, J. Am. Chem. Soc., vol 72 (1950), 2626–2629.

Reduction of alpha,alpha-dimethylalkanoic acids over copper chromite catalyst has been recited by Puzitskii et al., Neftekhimiya, vol. 7(2) (1967), 280–285. Reduction of methyl pivalate to neopentyl alcohol over copper chromite has been reported by Shutikova et al., Tr. Vses. Nauch.-Issled. Inst. Natur. Dushist. Veshchestv, no. 7 (1965), 16–20.

Catalytic reduction of acids, having branched structures, other than of the alpha,alpha,alpha-trisubstituted type, are disclosed by:

| U.S. Pat. No. 2,607,807 | Ford et al. |
| U.S. Pat. No. 3,478,112 | Adam et al. |
| U.S. Pat. No. 3,920,766 | Jubin, Jr. et al. |
| U.S. Pat. No. 4,433,175 | Kaufhold |

Hydrogenation of linear acids or their esters to corresponding alcohols as been disclosed in:

| U.S. Pat. No. 1,839,974 | Lazier |
| U.S. Pat. No. 2,091,800 | Adkins et al. |
| U.S. Pat. No. 2,110,483 | Guyer et al. |
| U.S. Pat. No. 2,275,152 | Lazier |
| U.S. Pat. No. 2,340,688 | Richardson et al. |
| U.S. Pat. No. 3,985,814 | Dougherty |
| U.S. Pat. No. 4,104,478 | Trivedi |
| U.S. Pat. No. 4,398,039 | Pesa et al. |
| U.S. Pat. No. 4,443,639 | Pesa et al. |
| Japan Patent 57032237-A | Sumitomo Chemical K.K. |
| German OLS 2,613,226 | Demmering (September 9, 1977) |
| WO 82/03854 | Davy McKee |
| Soviet Union Patent 899113 | Sultanov et al. |
| Vedage et al., J. Catalysis, vol. 77 (1982), page 558. | |

Of the foregoing, the Vedage et al. article discloses employing a copper/zinc oxide catalyst, normally used for methanol synthesis, to hydrogenate propanoic acid to propanol. The Davy McKee patent is of similar interest with respect to reduction of butyl butyrate or other esters. The reference contemplates reduction of branched esters, e.g., isobutyrates.

It is accordingly apparent that there is a need for improved syntheses of highly branched alkanols, particularly of the neoalkanol type, from readily available substrates such as neoacids, rather than from esters or other precursors.

DISCLOSURE OF INVENTION

In one aspect, this invention relates to a process for the synthesis of 1,1,1-trialkylalkanols of the formula $R_1R_2R_3CCH_2OH$ by hydrogenation of a neoacid of the formula $R_1R_2R_3CCOOH$, wherein $R_1$, $R_2$ and $R_3$ each are alkyl of 1–10 carbon atoms, at 175°–350° C. and a pressure of 10–100 Kg/cm² over a copper oxide/zinc oxide catalyst.

In another aspect, this invention relates to synthesis of neoalkanols from neoacids, using a nickel hydrogenation catalyst at 125°–200° C.

Catalytic hydrogenation of representative substrates for the practice of this invention may be expressed, in the case of pivalic acid, by the following equations:

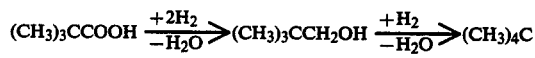

Neoacids are available commercially from the hydrocarboxylation of branched olefins (Koch reaction), as represented by the equation:

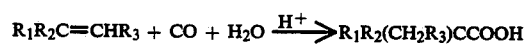

It is shown in the specification that representative neoacids, such as pivalic and neodecanoic acids, can be used as substrates.

Other types of neo-compounds, which can be used as alternative substrates, include corresponding neodiacids, or their esters.

It is preferred that the feed utilized in the practice of this invention is a neoacid, wherein alkyl is linear and $R_1$ and $R_2$ each are methyl. Most preferably, all three alkyls are methyl. Accordingly, the most preferred feed for the practice of this invention is pivalic acid. Pivalic acid is also known as neopentanoic acid, 2,2,2-trimethylacetic acid or 2,2-dimethylpropanoic acid.

A further preferred feed is known as neodecanoic acid, wherein $R_1$ and $R_2$ are methyl and $R_3$ is alkyl of six carbon atoms.

Products, obtained by the process of this invention include, in the case of pivalic acid, neopentanol and, in some cases, varying amounts of one or more of neopentane, isobutane and isopentane. Neopentane is also known as 2,2-dimethylpropane, 1,1,1-trimethylethane or tetramethylmethane. Isobutane is also known as 2-methylpropane and isopentane as 2-methylbutane. The isoparaffins, isolated as by-products from the process of this invention, are thought to originate by demethylation or isomerization of the feed or intermediates.

Operative conditions for the process of this invention, utilizing copper oxide/zinc oxide catalyst, are temperatures of 200°–350° C., hydrogen pressure of 10–100 $Kg/cm^2$, substrate feed rate of 0.1–1000 mM/g catalyst/h, and hydrogen feed rate of 75–8000 ml/g catalyst/h.

Preferred conditions, using a copper oxide/zinc oxide catalyst, are hydrogen pressures of 14–70 $Kg/cm^2$, temperatures of 225°–325° C., hydrogen flow rate of 1500–6000 ml/g catalyst/h and neoacid feed rate of 1.6–20 mM/g catalyst/h.

When a nickel hydrogenation catalyst is used, is preferred that a hydrogen feed rate of 1000–6000 ml/g catalyst/h, substrate feed rate of 0.1–1000 mM/g catalyst/h and pressure of 7–100 $Kg/cm^2$, be employed.

In carrying out neoalkanol synthesis according to this invention, difficulties can occur in handling neoacids, some of which are solids under the conditions used. In some cases, the feed can be diluted with a solvent, which is inert to the reaction condition and which has a boiling point, such that it can be readily removed from the product stream by distillation. Hydrocarbons and alcohols are representative of diluents which can be used when the catalyst is copper oxide/zinc oxide/alumina. Hydrocarbon solvents are preferred when a nickel hydrogenation catalyst is used. If a diluent is used, the preferred amount is 5–50% by weight of feed. A preferred alcoholic diluent is methanol and a preferred hydrocarbon diluent, hexane.

Alternatively, low melting neoacids can be melted and fed to the reactor in liquid form. Accordingly, use of undiluted feed is feasible and preferred.

Products, obtained by the process of this invention, can be purified by distillation or other well known techniques. Solid neoalcohols can be purified by recrystallization.

Catalysts, used in the process of this invention, are supported copper oxide/zinc oxide catalysts, of the type used in the synthesis of methanol by reaction between carbon monoxide and hydrogen. The binary copper/zinc oxide system is as described by Klier, "Methanol Synthesis," in *Advances in Catalysis*, vol. 31, Eley et al., editors, Academic Press, New York (1982), particularly at pages 258–271. These catalysts can be prepared on a variety of supports, such as, oxides of aluminum, silicon, zirconium, titanium, calcium, chromium or magnesium. The catalysts consist of coprecipitated CuO/ZnO, for example, from copper and zinc nitrate solutions. The compositional range employed is 12–66% as copper (II) oxide, 17–62% as zinc oxide and 4–38% carrier, e.g. alumina.

In high zinc catalysts, hydroxycarbonates are predominant, whereas in high copper catalysts, the main catalyst component is copper hydroxy nitrate, $Cu_2(OH)_3NO_3$. Calcination of either type of material in air at about 350° C. gave a mixture of Cu(II) oxide in the tenorite form and wurtzite zinc oxide. Reduction of these materials converted the copper (II) oxide to elemental copper, whereas the ZnO was unreduced. Accordingly, the catalysts are thought to be intimate mixtures of small particles of copper and zinc oxide.

A methanol synthesis catalyst, comprising copper and zinc oxide, supported on aluminum oxide, has been described by Stiles in Canadian Patent No. 1,021,354. This catalyst is thought to consist of copper oxide-zinc oxide having Cu:Zn ratios of 1:1 to 8:1, preferably about 4:1. The catalyst is relatively free of sodium or sulfur.

Other catalysts, appropriate for methanol synthesis and for the reactions of this invention are disclosed by Cornthwaite, U.S. Pat. No. 3,923,694; Davies et al., U.S. Pat. No. 3,961,037 and Dienes et al., U.S. Pat. No. 4,279,781, herein incorporated by reference. In addition, catalysts described by Vedage et al. or Davy McKee, supra, can be used.

It will be understood that, in the specification and claims, "copper oxide/zinc oxide" includes corresponding reduced forms, whether formed during activation or during the reactions of this invention.

Preferred copper oxide/zinc oxide catalysts for the utilization of this invention are those supported on alumina, more preferably those comprising 80–95% by weight of copper oxide/zinc oxide in 8:1-1: weight ratio and 20–5% by weight of alumina. Most preferred are catalysts, wherein the weight ratio of copper oxide/zinc oxide is 4:1 to 1:1.

The copper oxide/zinc oxide catalyst, used in the processes of this invention, is preferably activated by heating with 1–10% by volume of hydrogen in nitrogen at 250°–375° C. for 2–30 h.

Nickel hydrogenation catalysts, which can be used in the process of this invention, are supported nickel oxide catalysts. These can include nickel oxide catalysts, containing other oxides, including tungsten, cobalt, iron, magnesium and copper. The catalysts can be supported on alumina, silica, zirconia, titania, calcium oxide, chromium oxide, or mixtures thereof, as well as on kieselguhr. The compositional range is 2–75% by weight of nickel oxide and 98–25% by weight of carrier. Preferably the catalysts are supported on alumina and contain 10–50% weight of nickel or nickel oxide.

The nickel catalysts can be made by impregnating the support with a solution of a nickel salt, e.g., nickel nitrate or nickel acetate. The catalyst is then calcined. It is preferred that the nickel catalyst be activated by heating with 1–10% of hydrogen in nitrogen (by volume) at 250°–375° C. for 2 to 30 h. The catalysts can also be presulfided.

BEST MODE FOR CARRYING OUT THE INVENTION

Figure 1A:
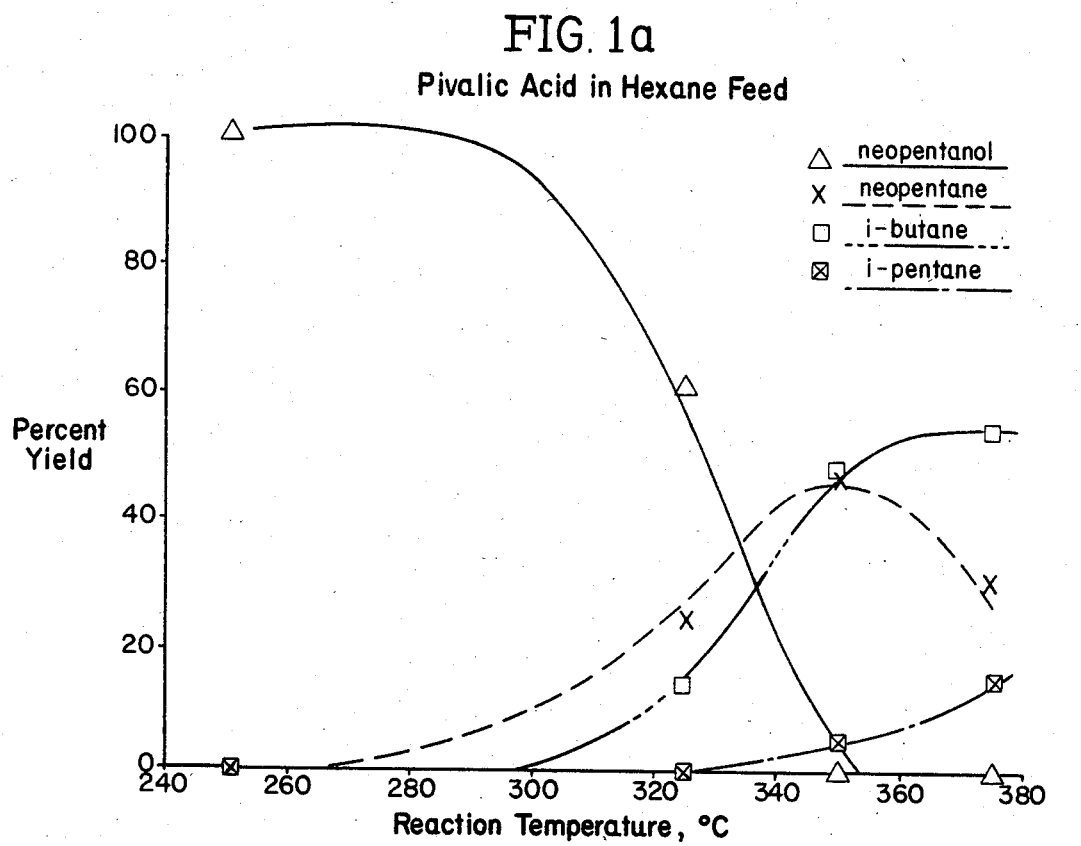
In FIGS. 1a and 1b is shown the relationship between reaction temperature and products obtained by hydrogenation of pivalic acid.

In a most preferred process for synthesizing neopentanol from pivalic acid, the reaction is carried out at over copper oxide/zinc oxide on alumina, at 225°–325° C. under a hydrogen feed rate of 1500–6000 ml/g catalyst/h and pivalic acid feed rate of 1.6–20 mM/g catalyst/h.

When nickel/alumina hydrogenation catalyst is used, it is preferred to do the hydrogenation at a hydrogen feed rate of 1000–6000 ml/g catalyst/h, substrate feed rate of 0.5–20 mM/g catalyst/h and pressure of 7–70 Kg/cm$^2$.

The pivalic acid is preferably diluted with 5–50% by weight of hexane or, with 5–50% by weight of methanol, when copper oxide/zinc oxide/alumina catalyst is used.

Most preferred catalysts are as recited above.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Experiments were done in a fixed-bed catalyst screening reactor, comprising a vertical tubular cylindrical 316 stainless steel tube (3.175 cm outer diameter, 0.30 cm wall thickness), inside of which was mounted a cylindrical quartz reactor (1.905 cm diameter), containing a catalyst bed 20 mm thick, packed above and below the catalyst bed with quartz wool. Gas was fed into the system from cylinders, pressure being controlled by back pressure regulators, in upflow fashion. Liquid was fed through a 0.16 cm stainless steel feedline downwardly into the quartz reactor. Liquid flow was controlled by a high pressure liquid pump. The temperature within the system was measured by a thermocouple located at the center of the catalyst bed. Product, removed from the system through a stainless steel tube at the bottom of the reactor system, was fed directly into an on-line gas chromatographic analyzer through a line heat traced at 175° C.

Hydrogenation catalyst (CuO/ZnO/alumina, unless otherwise indicated) pellets were ground in a porcelain mortar. A charge of 4.00 g of sieved catalyst (10–16 Taylor mesh fraction) was loaded into the quartz reactor and was reduced at a pressure of 5.6 Kg/cm$^2$ and 600 GHSV (STP) as follows:

1. under a stream of nitrogen, the temperature was increased from 30° C. to 250° C. at a rate of 0.5–5°/min
2. under a stream of hydrogen (2% by volume) in nitrogen, the temperature was held at 250° C. for 0–16 h;
3. under a stream of hydrogen (2% by volume) in nitrogen, the temperature was increased from 250° to 350°–375° C. at a rate of 0.5–1.5°/min and
4. catalyst was held at 350°–375° C. for 2–30 h in a stream of hydrogen (2% by volume) in nitrogen.

Product leaving the system was analyzed by gas chromatography, using a Perkin Elmer Sigma 2000, with a 0.32×15.24 cm. SS column packed with poropak Q. The carrier gas was helium and the flow rate was 30 ml/min. Flame ionization and hot wire detectors were employed. The injector was a Valco gas valve with a 1.0 ml gas loop at 200° C. The program used provided for a temperature increase of 15° C./min from 200°–250° C., after which the temperature was held at 250° C. for 10 min. A Perkin Elmer Data Station 3600 integrator was used to measure peak areas, generated by a flame ionization detector. An external standard of 0.5% neopentane by volume in nitrogen was used for determination of flame ionization detector response area to areas obtained from the product stream.

Material balance calculations compared the sum of mM of products to mM of substrate in the feed. Response factors and yields were calculated by the equations:

$$RF_{std} = \frac{FID_{std} \times 0.1}{[std]/(100 \times 22.4) \times MW_{std} \times (ml\ gas\ loop)}\ and$$

% product yield =

$$\frac{0.1}{RF_{std}} \times \frac{ml\ reactor\ exit\ flow/h \times 100}{mM\ substrate/h \times MW_{prod}} \times \frac{FID_{prod}}{ml\ gas\ loop}$$

wherein RF is the absolute response factor for 0.1 mg of standard compound in 1.0 ml of standard gas mixture at analysis conditions, using a flame ionization detector, [std] is the molar concentration of standard compound in the standard gas mix, MW is molecular weight and FID is measured flame ionization detector response in absolute area counts.

Other definitions, used in the Examples below, include:

catalyst selectivity for neopentanol: $\frac{mM\ neopentanol\ in\ product}{mM\ of\ products}$ percent substrate conversion: $\frac{mM\ products}{mM\ substrate\ in\ feed} \times 100$ percent neopentanol yield: $\frac{mM\ neopentanol\ in\ product}{mM\ substrate\ in\ feed} \times 100$ gas hourly space velocity (GHSV): $\frac{ml\ feed\ gas}{min} \times \frac{60}{g\ catalyst}$ Steady state conditions, unless otherwise indicated, were reached after two hours on line.

In the Examples, catalysts are generally defined by alumina content, the balance being CuO/ZnO or Ni in the stated weight ratio, before activation or reduction.

EXAMPLE 1

Pivalic acid in methanol (50.0% by weight of pivalic acid) was fed to a reactor charged with 4.00 g of 2:1 CuO/ZnO/10% alumina catalyst. The feed rate with respect to pivalic acid was 6.5 mM/h, the hydrogen flow rate 400 ml/min at STP, the pressure 70.3 Kg/cm$^2$ and the temperature 250° C. Under steady state conditions, the product contained 100 mol % of neopentanol. No unconverted pivalic acid was detected.

Experiments were done, as above, to determine the effect of reaction temperature on product distribution from pivalic acid feeds. The 2:1 CuO/ZnO/10% alumina catalyst was used. The rate of substrate feed was 1.6–2.2 mM/g catalyst/h, the hydrogen flow rate was 4500–6000 GHSV (ml/g catalyst/h) and the pressure 70.3 Kg/cm$^2$. Results at steady state operation for feeds, diluted with hexane or with methanol, are shown in Table 1 and in FIGS. 1a and 1b.

Figure 1B:
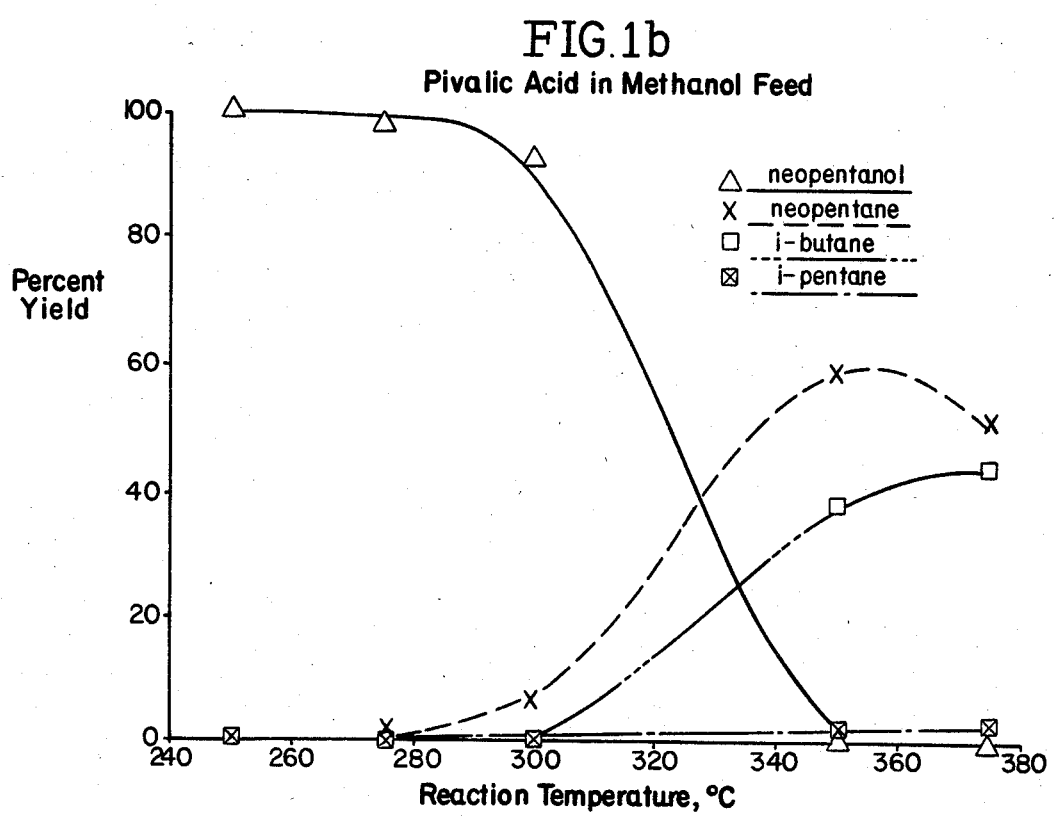

As shown in FIGS. 1a and 1b, pivalic acid was quantitatively converted to neopentanol at 250° C. At reaction temperatures of 325° C. and 350° C., pivalic acid was converted to hydrocarbons.

These experiments show that the neopentanol synthesis is preferably done at 325° C. or below, at the feed rates examined. These experiments further show that the solvent selected does not significantly affect the product mixture obtained.

EXAMPLE 2

Molten pivalic acid is used as substrate for hydrogenation at 250° C., feed rate of 6.5 mM/h, hydrogen flow rate of 400 ml/min and pressure of 70.3 pentanol yields increased with increasing substrate feed rates.

EXAMPLE 5

An experiment is run, otherwise as in Example 3(a), at a pivalic acid feed rate of 10 mM/g catalyst/h. Products contain more neopentanol and less hydrocarbons, than in Example 3(a).

TABLE 1

| Feed | GHSV Hydrogen | Feed Rate mM/g cat/hr | Temp °C. | % Yield | | | |
|---|---|---|---|---|---|---|---|
| | | | | NeoC₅OH | NeoC₅ | i-C₄ | i-C₅ |
| Pivalic | 6000 | 1.6 | 250 | 100 | 0 | 0 | 0 |
| acid/methanol | | | 275 | 98 | 2 | 0 | 0 |
| (50:50 wt.) | | | 300 | 93 | 7 | 0 | 0 |
| | | | 350 | 0 | 59 | 39 | 2 |
| | | | 375 | 0 | 52 | 45 | 3 |
| Pivalic | 4500 | 1.6 | 250 | 100 | 0 | 0 | 0 |
| acid/hexane | | | 325 | 61 | 25 | 14 | 0 |
| (80.6:19.4 wt.) | | | 350 | 0 | 47 | 48 | 5 |
| | | | 375 | 0 | 31 | 54 | 15 |

EXAMPLE 3

(a) Pivalic acid in hexane (80.6% by weight of pivalic acid) was hydrogenated over 2:1 CuO/ZnO/alumina catalyst (4.00 g), using a substrate feed rate of 6.5 mM/h, hydrogen flow rate of 300 ml/min at STP, pressure of 70.3 Kg/cm² and reaction temperature of 350° C. The products, under steady state operation, were 46 mol % of neopentane, 49 mol % of isobutane and 5 mol % of isopentane.

(b) An experiment, otherwise as in Example 3(a) was done at 325° C. and at a pressure of 35 Kg/cm². Higher yields of neopentanol are obtained. Lower yields of isobutane and neopentane and complete conversion of pivalic acid are obtained.

(c) The effect of reaction pressure on product distribution from feed consisting of pivalic acid/methanol (85.7:14.3 by weight) at 350° C., at a pivalic acid feed rate of 1.6 mM/h, was studied. The catalyst was 2:1 CuO/ZnO/10% alumina, using a hydrogen flow rate of 4500 GHSV and a pressure range of 35.2–70.3 Kg/cm². Results are shown in Table 2.

Complete conversion of pivalic acid to products occurred at 35.2–70.3 Kg/cm². At the lowest pressure used, some neopentanol was produced.

TABLE 2

Effect of Reaction Pressure on Product Distribution

| Kg/cm² Pressure | GHSV Hydrogen | % Yield | | | |
|---|---|---|---|---|---|
| | | Neo-pentanol | Neo-pentane | i-Butane | i-Pentane |
| 70.3 | 4500 | 0 | 52 | 47 | 1 |
| 35.2 | 4500 | 23 | 20 | 56 | 1 |
| 52.7 | 4500 | 0 | 38 | 60 | 2 |

TABLE 3

Effect of Pivalic Acid Feed Rate on Product Distribution

| Feed | Temp. | Feed Rate mM/g cat/hr | % Yield | | | |
|---|---|---|---|---|---|---|
| | | | Neopentanol | Neopentane | i-Butane | i-Pentane |
| Pivalic | 325° C. | 0.8 | 0 | 68 | 28 | 4 |
| acid/hexane | | 1.6 | 61 | 25 | 14 | 0 |
| (80.6:19.4 wt.) | | 3.2 | 76 | 14 | 10 | 0 |
| | | 6.4 | 84 | 8 | 8 | 0 |
| Pivalic | 350° C. | 0.2 | 0 | 68 | 25 | 7 |
| acid/methanol | | 0.4 | 0 | 70 | 26 | 4 |
| (83.2:16.8 wt.) | | 0.8 | 0 | 61 | 36 | 3 |
| | | 1.6 | 0 | 55 | 42 | 2 |
| | | 3.25 | 42 | 28 | 29 | 1 |
| | | 4.9 | 61 | 17 | 21 | 1 |

EXAMPLE 4

The effect of substrate feed rate on conversion and product distribution was studied using pivalic acid, admixed with methanol or with hexane. The experiments were done at 325° C. and 350° C., at a pressure of 70.3 Kg/cm², and hydrogen GHSV of 4500. The catalyst was 2:1 CuO/ZnO/10% alumina. Results are shown in Table 3.

At both of the temperatures studied, pivalic acid substrate was completely converted to products. Neo- (b) An experiment is done using pivalic acid in methanol (50% by weight) over a 2:1 CuO/ZnO/alumina catalyst (4.00 g) at a temperature of 325° C., hydrogen flow rate of 400 ml/g at STP, pressure of 70.3 Kg/cm² and substrate feed rate of 10.0 mM/g catalyst/h. Higher neopentanol yields are obtained than in runs, using lower feed rates.

EXAMPLE 6

The effect of variations in catalyst composition was studied, using 2:1 or 3:1 CuO/ZnO/10% alumina catalysts.

Reduction of pivalic acid was carried out at 70.3 Kg/cm² and 4500 GHSV for hydrogen, using pivalic acid, admixed with methanol or hexane, at a substrate feed rate of 1.6 mM/g catalyst/h. Results of these experiments are shown in Table 4.

It is apparent that, although the behavior of the catalysts is not identical, each of the catalysts gave similar product mixtures and that neopentanol was the major product at 325° C. It is therefore expected that a variety of CuO/ZnO/alumina catalysts can be used for carrying out the synthesis of this invention.

EXAMPLE 7

(a) Nickel on alumina catalyst was prepared by impregnating gammaalumina with an aqueous solution of nickel nitrate. The resulting catalyst (33% nickel) was extruded, calcined and reduced at 350° C. for 16 h under a stream of 2% hydrogen in nitrogen (by volume).

(b) The nickel/alumina catalyst (4.00 g, 33% Ni) was used for hydrogenation of pivalic acid (55% by weight in n-hexane) at 200° C., a pressure of 35 Kg/cm$^2$, hydrogen GHSV of 1500 and substrate feed rate of 1.1 mM/g catalyst/h. The products under steady state operation were 24 mol % of neopentanol, 11 mol % of neopentane, 3 mol % of isopentane, 40 mol % isobutane and traces of other hydrocarbons and unconverted pivalic acid.

This example shows that lower reaction temperatures result in formation of some neopentanol, but that, with the temperature and catalyst used, substantial demethylation occurs.

TABLE 4

Comparison of Hydrogenation Catalysts

| Feed | Reaction Temperature | Catalyst[a] | % Yield | | | |
|---|---|---|---|---|---|---|
| | | | Neo-pentanol | Neo-pentane | i-Butane | i-Pentane |
| A | 325° C. | 2:1 | 61 | 25 | 14 | 0 |
| B | | 3:1 | 48 | 31 | 20 | 1 |
| B | 350° C. | 2:1 | 0 | 51 | 47 | 2 |
| B | | 3:1 | 0 | 48 | 51 | 1 |

A Pivalic acid/hexane (80.6:19.4 wt.)
B Pivalic acid/methanol (85.7:14.3 wt.)
[a]Ratio indicates CuO/ZnO by weight, balance is alumina (10%)

EXAMPLE 8

Nickel/alumina catalyst of Example 7(a) (4.00 g) was used for hydrogenation of pivalic acid (55 weight % in n-hexane) at 175° C., a pressure of 14 Kg/cm$^2$, hydrogen flow rate of 1500 GHSV and substrate feed rate of 1.1 mM/g catalyst/h. The product contained 81 mol % of neopentanol, 13 mol % of unconverted pivalic acid and traces of other hydrocarbons.

This experiment shows that temperatures below 250° C., particularly in the presence of a nickel catalyst, favor formation of neopentanol, rather than further hydrogenation to hydrocarbons.

EXAMPLE 9

(a) Neodecanoic acid ($R_1$ and $R_2$ are methyl, $R_3$ is alkyl of six carbon atoms), diluted with 50% by weight of hexane, was hydrogenated at 375° C., pressure of 70.3 Kg/cm$^2$, hydrogen flow rate of 300 ml/min, and feed rate of 6 ml/h, over 4.00 g of 2:1 CuO/ZnO/10% alumina catalyst. The product under steady state conditions contained 29 mol % of neodecane, 6 mol % of neodecanol and 52 mol % of isononanes. The conversion to products was 88%.

(b) At a reaction temperature of 350° C. and pressure of 17.6 Kg/cm$^2$, the steady state product mixture from a run, otherwise as in Example 9(a), contained 0.3 mol % of neodecane, 5.2 mol % of neodecanol and 2.7 mol % of isononanes. Based on 8% conversion of the acid, selectivity toward neodecanol was 64%.

We claim:

1. In a process for the synthesis of a neoalcohol of the formula $R_1R_2R_3CCH_2OH$ by hydrogenation of a neoacid of the formula $R_1R_2R_3CCOOH$, wherein $R_1$, $R_2$ and $R_3$ are the same or different alkyl of 1–10 carbom atoms in the presence of a hydrogenation catalyst and hydrogen, the improvement which comprises hydrogenating said neoacid at a temperature from about 225° C. to about 325° C., a hydrogen flow rate of 1500 to 6000 ml/g catalyst/hr., a neoacid feed rate of 1.6 to 20 mM/g catalyst/hr. and a hydrogen pressure of 10 to 100 Kg/cm$^2$ over a copper oxide/zinc oxide catalyst comprising 80 to 95% by wt. of copper oxide/zinc oxide in an 8:1 to 1:1 weight ratio and 20 to 5% by weight alumina to obtain substantially complete conversion of the neoacid and at least 60 mol % yield of the corresponding neoalcohol.

2. The process of claim 1, wherein the copper oxide/zinc oxide is in a 4:1 to 1:1 weight ratio.

3. The process of claim 1, wherein alkyl is linear and $R_1$ and $R_2$ are methyl.

4. The process of claim 1, wherein $R_1$, $R_2$ and $R_3$ are methyl.

5. The process of claim 2, wherein $R_1$, $R_2$ and $R_3$ are methyl.

6. The process of claim 1, wherein the neoacid is diluted with 5–50% by weight of hexane.

7. The process of claim 1, wherein the neoacid feed is diluted with 5–50% by weight of methanol.

8. The process of claim 1, wherein the neoacid is undiluted.

9. The process of claim 1, wherein the catalyst is activated by treatment with 1–10% by volume of hydrogen in nitrogen at 250°–375° C. for 2–30 h.

10. The process of claim 1, wherein $R_1$ and $R_2$ are methyl and $R_3$ is alkyl of six carbon atoms.

* * * * *